(12) United States Patent
Seong et al.

(10) Patent No.: US 10,473,588 B2
(45) Date of Patent: Nov. 12, 2019

(54) DEVICE AND METHOD FOR WATER-PROOFING TEST

(71) Applicants: HYUNDAI MOTOR COMPANY, Seoul (KR); KIA MOTORS CORPORATION, Seoul (KR)

(72) Inventors: Ha Seung Seong, Daejeon (KR); Jin Seok Kim, Yongin-si (KR)

(73) Assignees: Hyundai Motor Company, Seoul (KR); KIA Motors Corporation, Seoul (KR)

( * ) Notice: Subject to any disclaimer, the term of this patent is extended or adjusted under 35 U.S.C. 154(b) by 0 days.

(21) Appl. No.: 16/167,153

(22) Filed: Oct. 22, 2018

(65) Prior Publication Data

US 2019/0154573 A1 May 23, 2019

(30) Foreign Application Priority Data

Nov. 17, 2017 (KR) .................. 10-2017-0154064

(51) Int. Cl.
| | |
|---|---|
| G01N 21/3581 | (2014.01) |
| F26B 25/22 | (2006.01) |
| G01N 21/3554 | (2014.01) |
| G01M 3/00 | (2006.01) |

(52) U.S. Cl.
CPC ......... *G01N 21/3581* (2013.01); *F26B 25/22* (2013.01); *G01M 3/00* (2013.01); *G01N 21/3554* (2013.01)

(58) Field of Classification Search
CPC .. G01N 21/3581; G01N 21/3554; F26B 25/22

USPC ....................................................... 250/339.1
See application file for complete search history.

(56) References Cited

U.S. PATENT DOCUMENTS

| | | | |
|---|---|---|---|
| 9,080,961 B2 | 7/2015 | Adachi | |
| 2008/0186239 A1* | 8/2008 | Itsuji | H01Q 9/28 343/700 MS |
| 2009/0152475 A1* | 6/2009 | Sasaki | G01J 3/10 250/492.1 |
| 2011/0100967 A1* | 5/2011 | Yoo | B23K 26/032 219/121.73 |
| 2011/0133090 A1* | 6/2011 | Demers | G01N 21/3586 250/339.07 |
| 2011/0198501 A1* | 8/2011 | Ouchi | A61B 5/0059 250/343 |
| 2011/0299066 A1* | 12/2011 | Kusukame | G01N 21/19 356/51 |
| 2012/0068090 A1* | 3/2012 | Park | H01S 5/06258 250/493.1 |

(Continued)

FOREIGN PATENT DOCUMENTS

| | | |
|---|---|---|
| JP | 2011-220901 A | 11/2011 |
| JP | 2013-186022 A | 9/2013 |

*Primary Examiner* — Taeho Jo
(74) *Attorney, Agent, or Firm* — Brinks Gilson & Lione

(57) ABSTRACT

The present disclosure provides a device for a water-proofing test, the device including: a terahertz wave oscillator configured to generate and oscillate a terahertz wave; a terahertz wave detector configured to detect the terahertz wave reflected from a predetermined test area of a test target or transmitted through the predetermined test area; and a controller configured to analyze a frequency spectrum of the terahertz wave to determine whether water is penetrated into the predetermined test area.

17 Claims, 8 Drawing Sheets

(56) References Cited

U.S. PATENT DOCUMENTS

| | | | | |
|---|---|---|---|---|
| 2012/0181431 A1* | 7/2012 | Mitin | ............... | G01N 21/3581 |
| | | | | 250/338.4 |
| 2012/0273681 A1* | 11/2012 | Schulkin | ............ | G01J 3/0291 |
| | | | | 250/339.06 |
| 2013/0212904 A1* | 8/2013 | Adachi | ................ | B29B 13/08 |
| | | | | 34/573 |
| 2015/0060673 A1* | 3/2015 | Zimdars | ............. | G01S 17/88 |
| | | | | 250/341.2 |
| 2017/0336260 A1* | 11/2017 | Fujihara | ................ | G01J 3/28 |
| 2017/0336261 A1* | 11/2017 | Fujihara | ................ | G01J 3/42 |
| 2019/0117109 A1* | 4/2019 | Grundfest | ............ | G01B 11/24 |

\* cited by examiner

DEVICE AND METHOD FOR WATER-PROOFING TEST

CROSS-REFERENCE TO RELATED APPLICATION

This application claims priority to and the benefit of Korean Patent Application No. 10-2017-0154064, filed on Nov. 17, 2017, which is incorporated herein in its entirety by reference.

TECHNICAL FIELD

The present disclosure relates to a device and a method for a water-proofing test to test a water-proofing state of an object to be tested.

BACKGROUND

The statements in this section merely provide background information related to the present disclosure and may not constitute prior art.

Generally, vehicles are subjected to a water-proofing test in a shower booth provided in a manufacturing line or other place. In the shower booth, high-pressure water is sprayed to a vehicle, and a water-proofing test is carried out on the vehicle to which the high-pressure water has been sprayed.

Conventionally, the water-proofing test is performed such that a worker determines whether water has penetrated into a vehicle by directly observing the vehicle with his or her naked eye. Generally, however, water penetrating into a vehicle mainly stays in a portion which is hard to observe from the outside, such as a gap between a vehicle body frame and various protective layers provided to cover the vehicle body frame. Therefore, with the conventional method for a water-proofing test, it is difficult to accurately test water-proofing performance of a vehicle.

SUMMARY

One form of the present disclosure provides a device and a method for a water-proofing test, improved to accurately test the water-proofing performance of an object to be tested (or a test target).

Another form of the present disclosure provides a device and a method for a water-proofing test, improved to test a test target in a non-destructive state as to whether water has penetrated into the test target.

In some forms of the present disclosure, a device for a water-proofing test may include: a terahertz wave oscillator generating and oscillating a terahertz wave; a terahertz wave detector detecting the terahertz wave reflected from a predetermined test area of a test target or transmitted through the test area; and a controller analyzing a frequency spectrum of the terahertz wave detected by the terahertz wave detector to determine whether water has penetrated into the test area.

The device may further include an evaporator applying heat to the test area such that the water which has penetrated into the test area is evaporated to be phase-transformed into water vapor.

The evaporator may include: a guide laser beam oscillator generating and oscillating a guide laser beam for evaporating the water; and a guide laser beam irradiator irradiating the guide laser beam to the test area.

The terahertz wave oscillator may oscillate the terahertz wave in a state in which the heat is applied to the test area by the evaporator.

The controller may determine whether water has penetrated into the test area by comparing power of the terahertz wave at at least one peak frequency where a rate of absorption of the terahertz wave by the water vapor is higher than or equal to a predetermined reference rate with power of the terahertz wave in the other remaining frequency bands excluding the at least one peak frequency.

The controller may control the terahertz wave oscillator such that a frequency of the terahertz wave is converted within a predetermined frequency band including the at least one peak frequency.

The controller may determine whether water has penetrated into the test area on the basis of power of the terahertz wave at at least one peak frequency where a rate of absorption of the terahertz wave by the water vapor is higher than or equal to a predetermined reference rate.

The terahertz wave oscillator may include: a dual mode laser beam oscillator generating and oscillating a pair of distributed feedback laser beams having different wavelengths; and a terahertz wave emitter generating and oscillating the terahertz wave upon receiving the distributed feedback laser beams.

The terahertz wave detector may include a terahertz wave receiver converting the terahertz wave reflected from the test area or transmitted through the test area into an electrical signal and oscillating the converted electrical signal.

The terahertz wave detector may further include a signal amplifier amplifying the electrical signal and transmitting the amplified electrical signal to the controller.

The terahertz wave detector may further include a terahertz wave collector collecting the terahertz wave reflected from the test area or transmitted through the test area and transmitting the collected terahertz wave to the terahertz wave receiver.

The terahertz wave collector may be an integrating sphere formed of a material capable of reflecting the terahertz wave and having a predetermined radius of curvature, and the terahertz wave receiver may be positioned at a focal point of the terahertz wave collector.

In some forms of the present disclosure, a method for a water-proofing test may include steps of: (a) applying heat to a predetermined test area of a test target such that water penetrating into the test area is evaporated to be phase-transformed into water vapor; (b) irradiating a terahertz wave to the test area; and (c) analyzing the terahertz wave reflected from the test area or transmitted through the test area to determine whether water has penetrated into the test area.

The method may further include step (d) obtaining a frequency spectrum of the terahertz wave reflected from the test area or transmitted through the test area, step (d) being performed between step (b) and step (c), wherein step (c) may be performed by determining whether water has penetrated into the test area through analysis of the frequency spectrum of the terahertz wave.

Step (a) may be performed by irradiating a guide laser beam for evaporating the water to the test area.

Step (b) may be performed by converting a frequency of the terahertz wave within a predetermined frequency band including at least one peak frequency where a rate of absorption of the terahertz wave by the water vapor is higher than or equal to a predetermined reference rate.

Step (c) may be performed by determining whether water has penetrated into the test area by comparing power of the terahertz wave at the at least one peak frequency with power of the terahertz wave in the other remaining frequency bands excluding the at least one peak frequency.

Step (c) may be performed by determining whether water has penetrated into the test area on the basis of power of the terahertz wave at the at least one peak frequency.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
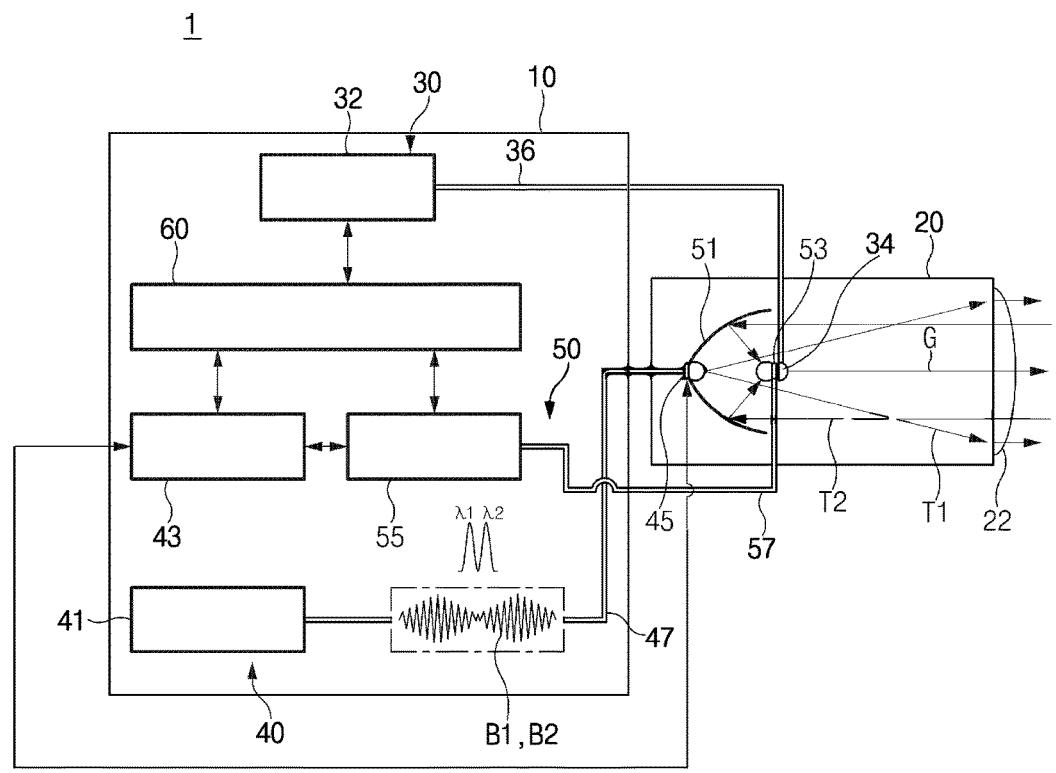
FIG. 1 illustrates the configuration of a device for a water-proofing test, in one form of the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Hereinafter, exemplary forms of the present disclosure will be described in detail with reference to the accompanying drawings. In the drawings, the same reference numerals will be used throughout to designate the same or equivalent elements. In addition, a detailed description of well-known techniques associated with the present disclosure will be ruled out in order not to unnecessarily obscure the gist of the present disclosure.

Terms such as first, second, A, B, (a), and (b) may be used to describe the elements in exemplary forms of the present disclosure. These terms are only used to distinguish one element from another element, and the intrinsic features, sequence or order, and the like of the corresponding elements are not limited by the terms. Unless otherwise defined, all terms used herein, including technical or scientific terms, have the same meanings as those generally understood by those with ordinary knowledge in the field of art to which the present disclosure belongs. Such terms as those defined in a generally used dictionary are to be interpreted as having meanings equal to the contextual meanings in the relevant field of art, and are not to be interpreted as having ideal or excessively formal meanings unless clearly defined as having such in the present application.

Figure 2:
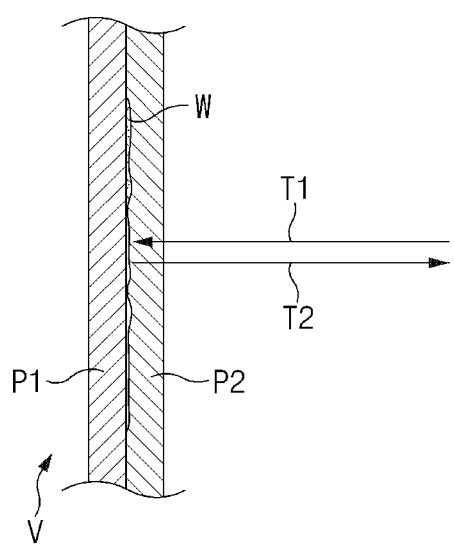
FIG. 2 illustrates a state in which water penetrates into a vehicle.
Figure 3:
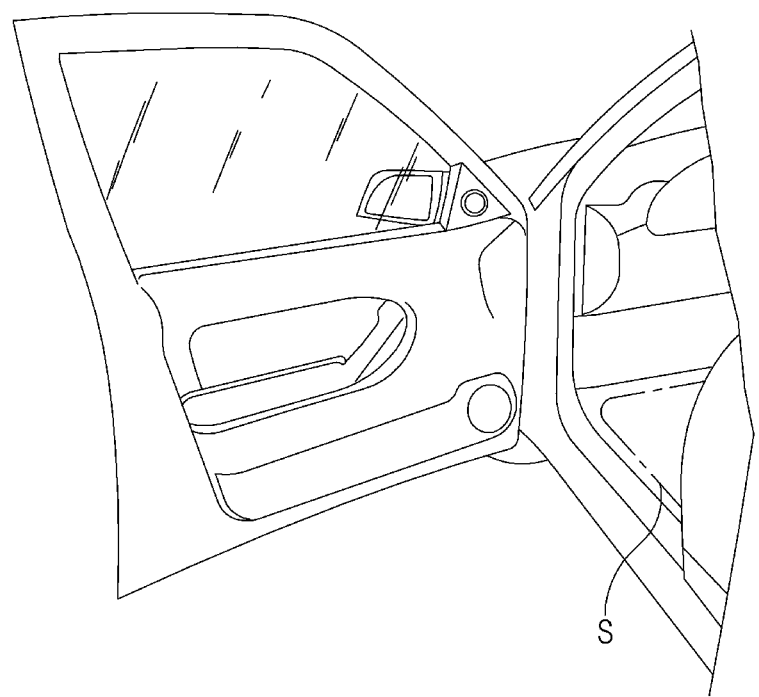
FIGS. 3 and 4 illustrate main water-proofing test target portions of a vehicle.
Figure 4:
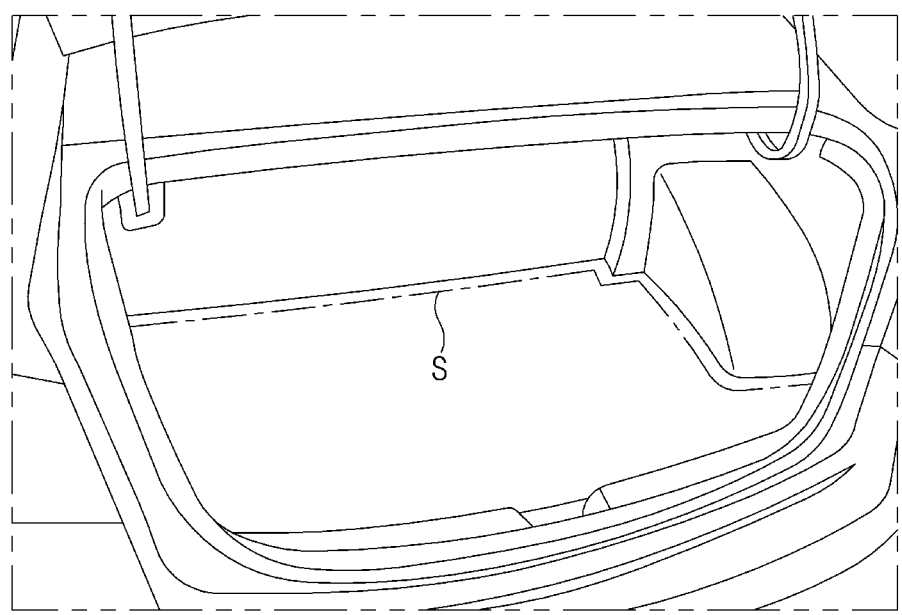

FIG. 1 illustrates the configuration of a device for a water-proofing test in some forms of the present disclosure, FIG. 2 illustrates a state in which water penetrates into a vehicle, and FIGS. 3 and 4 illustrate main water-proofing test target portions of a vehicle.

Referring to FIG. 1, a device 1 for a water-proofing test (or a water-proofing test device 1), in some forms of the present disclosure, may include a main body 10 for providing space for installation of a power source, analysis equipment, and the like, necessary for a water-proofing test, a measurement probe 20 for providing an operation unit of the water-proofing test device 1, an evaporator 30 applying heat to a predetermined test area A of an object P to be tested (or test target P) such that water penetrating into the test area A evaporates to be phase-transformed into water vapor, a terahertz wave oscillator 40 generating and oscillating a terahertz wave, a terahertz wave detector 50 detecting a terahertz wave reflected from the test area A, and a controller 60 analyzing a frequency spectrum of the terahertz wave detected by the terahertz wave detector 50 to determine whether water has penetrated into the test area A. For the purposes of description, hereinafter, the terahertz wave before being reflected from the test area A will be referred to as "T1" and the terahertz wave after being reflected from the test area A will be referred to as "T2".

The controller 60 includes a processor and a memory. The processor may be programmed to receive instructions stored in the memory and to analyze a frequency spectrum of the terahertz wave detected by the terahertz wave detector 50. The memory may be a data store, e.g., a hard disk drive, a solid-state drive, a server, or any volatile or non-volatile media. The memory may store the data collected by the terahertz wave detector 50.

The water-proofing test device 1 may perform a water-proofing test on the test area A by irradiating the terahertz wave T1 onto the predetermined test area A of the test target P and subsequently tracking reflection, transmission, and absorption phenomena of the terahertz wave T1, occurring in the test area A. A kind of the test target P that may be subjected to the water-proofing test using the water-proofing test device 1 is not particularly limited. For example, the test target P may be a vehicle.

Referring to FIG. 2, when an abnormality occurs in water-proofing performance of a vehicle, water penetrating into the vehicle from the outside flows along a vehicle body frame P1 such as a dash panel, a roof panel, and a side assy panel, and mainly stays in a gap between the vehicle body frame P1 and at least one protective layer P2 stacked to cover the vehicle body frame P1.

Generally, the vehicle body frame P1 is mainly formed of a conductive material, such as a metal material, totally reflecting the terahertz wave T1, and the protective layer P2 is manly famed of a non-conductive material, such as a synthetic resin material, allowing the terahertz wave T1 to be transmitted therethrough. Therefore, when the terahertz wave T1 is irradiated to a specific portion V of the vehicle in which the vehicle body frame P1 and the protective layer P2 are laminated, a terahertz wave T1 transmission phenomenon occurs in the protective layer P2 and a terahertz wave T1 reflection phenomenon occurs in the vehicle body frame P1. For example, as illustrated in FIG. 2, the terahertz wave T1 irradiated to one surface of the specific portion V is transmitted through the protective layer P2 and is incident on the vehicle body frame P1, and the terahertz wave T2 incident on the vehicle body frame P1 is reflected from the vehicle body frame P1 and is then transmitted through the protective layer P2 so as to be emitted from one surface of the specific portion V.

However, water or water vapor has properties of absorbing the terahertz wave T1. Thus, the water-proofing test device 1 may test the water-proofing performance of the vehicle by irradiating the terahertz wave T1 to the specific portion V and subsequently detecting whether the terahertz wave absorption phenomenon of water occurs in the specific portion V. As illustrated in FIGS. 3 and 4, the water-proofing test device 1 may test the water-proofing performance of the vehicle by selectively irradiating the terahertz wave T1 along a portion S anticipated for water penetrating into the vehicle from the outside to mainly stay due to a structural factor such as a slope. A water-proofing test method using the terahertz wave T1 absorption phenomenon of water will be described below in more detail.

As illustrated in FIG. 1, the main body 10 may be provided with a guide laser beam oscillator 32 of the evaporator 30, a dual mode laser beam oscillator 41 and a signal modulator 43 of the terahertz wave oscillator 40, a signal amplifier 55 of the terahertz wave detector 50, the controller 60, and the like. The main body 10 may be provided with a battery (not shown) that provides power for driving the water-proofing test device 1.

When the water-proofing test is performed on a vehicle by the water-proofing test device 1, the main body 10 may be fixed to one side of a shower booth, but an installation position of the main body 10 is not limited thereto.

Figure 5:
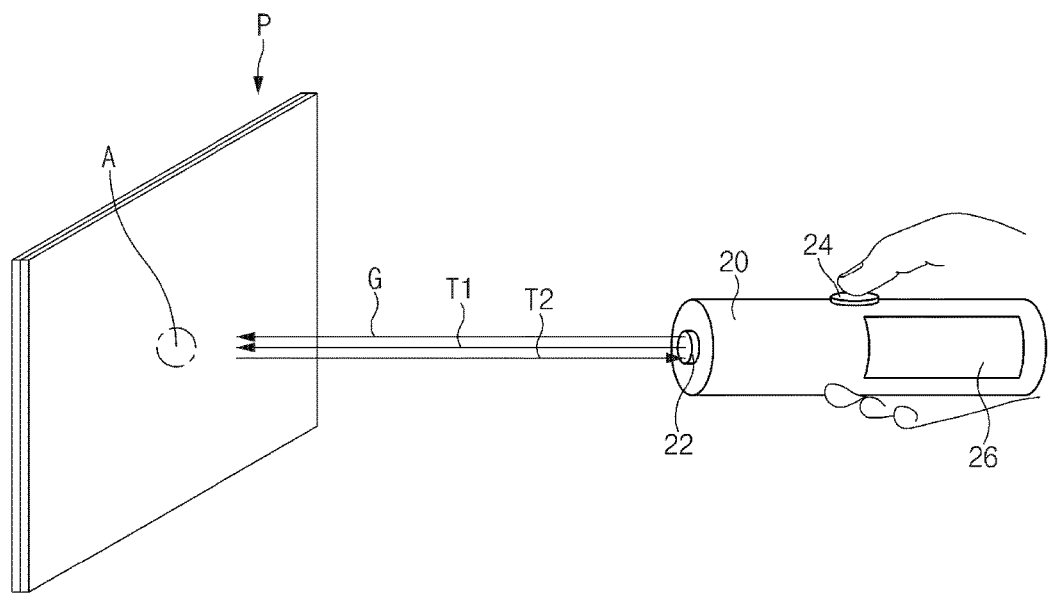
FIG. 5 illustrates a state in which a guide laser beam and a terahertz wave are irradiated to a test area of an object to be tested by a measurement probe illustrated in FIG. 1.

FIG. 5 illustrates a state in which a guide laser beam and a terahertz wave are irradiated to a test area of an object to be tested by the measurement probe illustrated in FIG. 1.

As illustrated in FIG. 1, the measurement probe 20 may be provided with a guide laser beam irradiator 34 of the evaporator 30, a terahertz wave transmitter 45 of the terahertz wave oscillator 40, and a terahertz wave collector 51 and a terahertz wave receiver 53 of the terahertz wave detector 50.

As illustrated in FIGS. 1 and 5, the measurement probe 20 may include a focus lens 22 for adjusting the focus of the terahertz wave T1 and a guide laser beam G, at least one button 24 for controlling the driving of the water-proofing test device 1, and a display unit 26 for displaying information such as a water-proofing test result.

The measurement probe 20 may have a shape allowing an operator to easily grip the measurement probe 20. For example, as illustrated in FIG. 5, the measurement probe 20 may have a cylindrical shape. Thus, as illustrated in FIG. 5, the operator, in a state of gripping the measurement probe 20, may operate the measurement probe 20 such that the guide laser beam G and the terahertz wave T1 are irradiated to the test area A.

The evaporator 30 may apply heat to the test area A such that water penetrating into the test target P from the outside and staying in the test target A (hereinafter, referred to as "water penetrating into the test area A") may be evaporated to be transformed into water vapor.

Referring to FIG. 5, water vapor has properties that an energy absorption rate with respect to a terahertz wave of a specific frequency that belongs to a terahertz frequency band is significantly higher than an energy absorption rate with respect to a terahertz wave of the other remaining frequencies that belong to the terahertz frequency band. That is, when the terahertz wave is irradiated to water vapor, there is an energy absorption peak where energy of the terahertz wave is absorbed by water vapor at a remarkably high rate at the specific frequency, which is different from a case where the terahertz wave is irradiated to liquid water. Therefore, when the water-proofing test is performed in a state in which water penetrating into the test area A is phase-transformed to water vapor, whether water has penetrated into the test area A may be more accurately tested by tracking whether the energy absorption peak is present. By taking this into consideration, the water-proofing test device 1 includes the evaporator 30 capable of applying heat to the test area A such that water penetrating into the test area A may be evaporated. For convenience of explanation, the specific frequency will be referred to as a peak frequency.

The structure of the evaporator 30 is not particularly limited. For example, as illustrated in FIG. 1, the evaporator 30 may include the guide laser beam oscillator 32 for generating and oscillating the guide laser beam G for evaporating water penetrating into the test area A, and the guide laser beam irradiator 34 for irradiating the guide laser beam G oscillated from the guide laser beam oscillator 32 to the test area A.

The guide laser beam oscillator 32 may be installed inside the main body 10 as illustrated in FIG. 1, but is not limited thereto. An output of the guide laser beam oscillator 32 may be adjusted such that only water penetrating into the test area A may be selectively evaporated without damaging the test area A. The guide laser beam G oscillated from the guide laser beam oscillator 32 may be transferred to the guide laser beam irradiator 34 by a waveguide 36 provided to connect the guide laser beam oscillator 32 and the guide laser beam irradiator 34. However, the present disclosure is not limited thereto, and the guide laser beam G may be transferred to the guide laser beam irradiator 34 by an optical path changing member, such as at least one reflector, installed between the guide laser beam oscillator 32 and the guide laser beam irradiator 34.

The guide laser beam irradiator 34 may be installed inside the measurement probe 20 as illustrated in FIG. 1, but is not limited thereto. The guide laser beam irradiator 34 may be provided to irradiate the guide laser beam G received through the waveguide 36 to the test area A. The guide laser beam irradiator 34 may be a condenser lens capable of condensing the guide laser beam G toward the test area A. For example, the guide laser beam irradiator 34 may be formed of a collimation lens capable of shaping the guide laser beam G to parallel light. As illustrated in FIG. 5, the guide laser beam G having passed through the guide laser beam irradiator 34 may be adjusted in focus by the focus lens 22 of the measurement probe 20 and subsequently irradiated to the test area A. Thus, when water penetrates into the test area A, the water may be evaporated by heat applied by the guide laser beam G and phase-transformed to water vapor. For example, when the test target P is a vehicle, water penetrating into an inner portion of the predetermined test area A of the vehicle, such as a gap between the vehicle body frame P1 and the protective layer P2, may be evaporated by the guide laser beam G so as to be phase-transformed to water vapor, and the generated water vapor may be received in the test area A.

Figure 6:
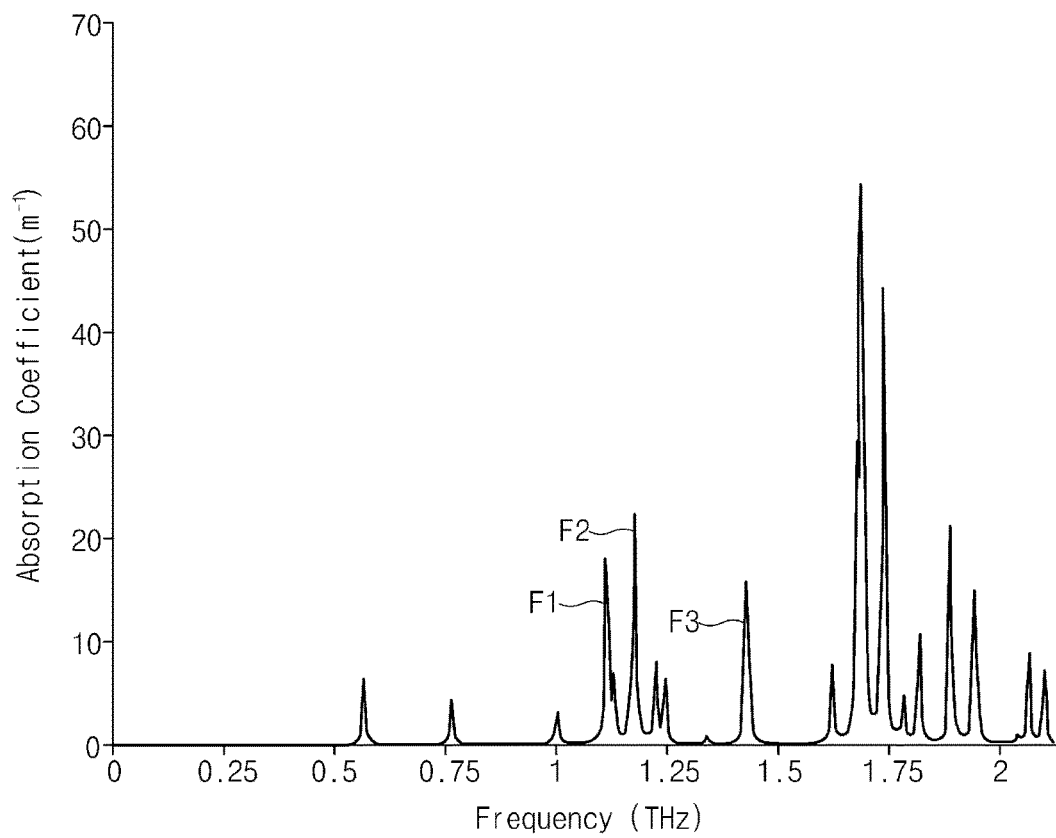
FIG. 6 illustrates a graph for explaining a peak frequency.

FIG. 6 illustrates a graph for explaining a peak frequency.

The terahertz wave oscillator 40 may be provided to generate the terahertz wave T1 for testing wafer-proofing performance of the test target P and oscillate toward the test area A.

The structure of the terahertz wave oscillator 40 is not particularly limited. For example, as illustrated in FIG. 1, the terahertz wave oscillator 40 may include the dual mode laser beam oscillator 41 for generating and oscillating a pair of distributed feedback laser beams B1 and B2, the signal modulator 43 for outputting a modulated signal for canceling noise included in a terahertz wave, and the terahertz wave transmitter 45 receiving the distributed feedback laser beams B1 and B2 oscillated from the dual mode laser beam oscillator 41 and generating and oscillating the terahertz wave T1.

The dual mode laser beam oscillator 41 may be installed inside the main body 10 as illustrated in FIG. 1, but is not limited thereto. The dual mode laser beam oscillator 41 may generate the pair of distributed feedback laser beams B1 and B2 having different wavelengths $\lambda 1$ and $\lambda 2$, respectively, and beat and oscillate the generated distributed feedback laser beams B1 and B2.

A frequency of the terahertz wave T1 generated by the terahertz wave transmitter 45 to be described later may be proportional to a difference between the wavelength $\lambda 1$ of any one distributed feedback laser beam B1 and the wavelength $\lambda 2$ of the other distributed feedback laser beam B2. Therefore, the dual mode laser beam oscillator 41 may selectively change at least one of the wavelengths $\lambda 1$ and $\lambda 2$ of the distributed feedback laser beams B1 and B2 in order to selectively adjust the frequency of the terahertz wave T1 in the terahertz frequency band including at least one of peak frequencies F1, F2, and F3. Since the technique of selectively changing the frequency of the terahertz wave T1 is generally used in the field of terahertz waves, a detailed description thereof will be omitted.

As illustrated in FIG. 1, the distributed feedback laser beams B1 and B2 beat and oscillated from the dual mode laser beam oscillator 41 may be transferred to the terahertz wave transmitter 45 through a waveguide 47 provided to connect the dual mode laser beam oscillator 41 and the terahertz wave transmitter 45. However, the present disclosure is not limited thereto, and the distributed feedback laser beams B1 and B2 may be transferred to terahertz wave transmitter 45 by an optical path changing member, such as at least one reflector, installed between the dual mode laser beam oscillator 41 and the terahertz wave transmitter 45.

The signal modulator 43 may generate a modulated signal for canceling noise included in the terahertz wave, and transmit the generated modulated signal to the terahertz wave transmitter 45 and the signal amplifier 55 of the terahertz wave detector 50. The terahertz wave transmitter 45 may generate and oscillate the terahertz wave T1 modulated by the modulated signal, and the signal amplifier 55 may cancel noise included in the terahertz wave T2 reflected from the test area A using the modulated signal directly transmitted from the signal modulator 43. Since the technique of canceling noise of the electromagnetic wave using the modulated signal is generally used in the field of electromagnetic waves, a detailed description thereof will be omitted.

As illustrated in FIG. 1, the terahertz wave transmitter 45 may be installed inside the measurement probe 20. Using the distributed feedback laser beams B1 and B2 transmitted through the waveguide 47 in a beat state and a DC bias applied to the terahertz wave transmitter 45, the terahertz wave transmitter 45 may generate and oscillate the terahertz wave T1 proportional to the difference between the wavelength $\lambda 1$ of one distributed feedback laser beam B1 and the wavelength $\lambda 2$ of the other distributed feedback laser beam B2.

More specifically, an electron-hole pair may be generated in a photoconductor thin film (not shown) of the terahertz wave transmitter 45 when the beat distributed feedback laser beams B1 and B2 are incident between antenna electrodes (not shown) to which a DC bias of −5 V to −1 V is applied.

Then, when the beat distributed feedback laser beams B1 and B2 are transferred to the terahertz wave transmitter 45, a photocurrent is generated as photocharges are transferred to the electrodes (not shown) by the DC bias. Such a photocurrent flows for a very short period of time, and an electromagnetic wave is formed due to a change in the photocurrent. However, when a transfer time of the photocharges is as short as a picosecond level, the electromagnetic wave becomes a terahertz wave T1. Since the technique of generating the terahertz wave T1 as described above is generally used in the field of terahertz waves, a detailed description thereof will be omitted.

As illustrated in FIG. 5, the terahertz wave T1 oscillated from the terahertz wave transmitter 45 may be irradiated to the test area A in a state of being adjusted in focus by the focusing lens 22 of the measurement probe 20, and subsequently reflected from the test area A.

Meanwhile, the controller 60 may control the evaporator 30 and the terahertz wave oscillator 40 such that the terahertz wave T1 may be irradiated to the test area A in a state in which water penetrating into the test area A is evaporated in advance by the guide laser beam G. For example, the controller 60 may control a driving timing of the evaporator 30 and the terahertz wave oscillator 40 such that the terahertz wave T1 may be irradiated to the test area A when a predetermined standby time has lapsed since the irradiation of the guide laser beam G to the test area A. Then, the terahertz wave T1 irradiated to the test area A may be absorbed by water vapor generated by the evaporator 30 at an absorption rate corresponding to the frequency of the terahertz wave T1, in the process of being reflected from the test area A.

Here, the terahertz wave T1 may not be observed with the naked eye, while the guide laser beam G may be observed with the naked eye. Therefore, the operator may recognize whether the terahertz wave T1 is normally irradiated to the test area A by observing a state in which the guide laser beam G is irradiated to the test area A with the naked eye. That is, the guide laser beam G may serve to assist the terahertz wave T1 to be accurately irradiated to the test area A, as well as serving as a heat source for evaporating water penetrating into the test area A.

The controller 60 may include a microprocessor or central processing unit, a read only memory (ROM), a random access memory (RAM), an electrically programmable read only memory (EPROM), a high speed clock, and the like.

Figure 7:
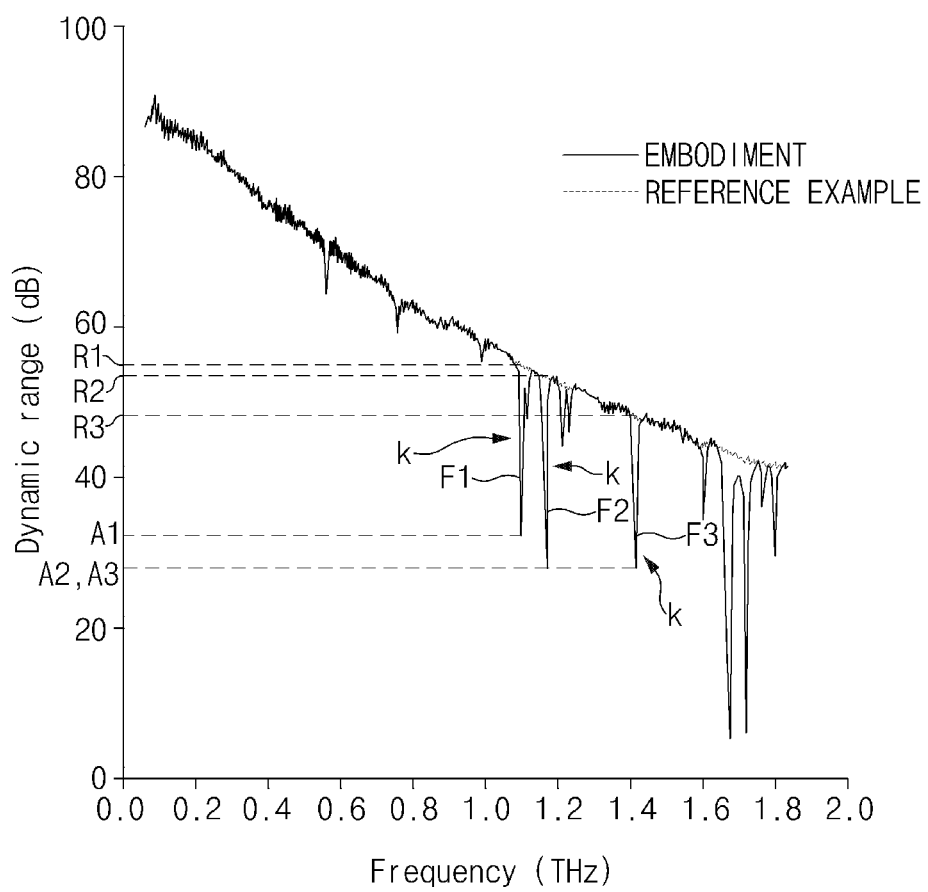
FIG. 7 illustrates a graph of a frequency spectrum of a terahertz wave.

FIG. 7 illustrates a graph of a frequency spectrum of a terahertz wave.

The terahertz wave detector 50 may be provided to detect the terahertz wave T2 reflected from the test target P.

The structure of the terahertz wave detector 50 is not particularly limited. For example, as illustrated in FIG. 1, the terahertz wave detector 50 may include the terahertz wave collector 51 provided to collect the terahertz wave T2 reflected from the test target P, the terahertz wave receiver 53 for converting the terahertz wave T2 received from the terahertz wave collector 51 into an electrical signal and oscillating the electrical signal, and the signal amplifier 55 for amplifying the electrical signal received from the terahertz wave receiver 53 and transmitting the amplified signal to the controller 60.

The terahertz wave collector 51 may be positioned on an optical path of the terahertz wave T2 reflected from the test area A. For example, as illustrated in FIG. 1, the terahertz wave collector 51 may be installed inside the measurement probe 20 such that the terahertz wave T2 reflected from the test area A may be incident thereon.

The structure of the terahertz wave collector 51 is not particularly limited. For example, the terahertz wave collector 51 may be an integrating sphere formed of a material capable of reflecting the terahertz wave T2 and having a predetermined radius of curvature. Then, as illustrated in FIG. 1, the terahertz wave collector 51 may reflect the terahertz wave T2 incident on the terahertz wave collector 51 into a focal point formed in a position corresponding to the radius of curvature of the terahertz wave collector 51.

The terahertz wave receiver 53 may be installed inside the measurement probe 20 such that it may be located at a focal point of the terahertz wave collector 51 as illustrated in FIG. 1. Using the terahertz wave T2 received from the terahertz wave collector 51, the terahertz wave receiver 53 may generate and oscillate the electrical signal corresponding to the terahertz wave T2.

More specifically, an electron-hole pair may be generated in a photoconductor thin film of the terahertz wave receiver 53. When the terahertz wave T2 is incident on the terahertz wave receiver 53, the photocharges may be transferred to the electrodes due to an electromagnetic field of the terahertz wave T2 to generate a photocurrent, i.e., the electrical signal corresponding to the terahertz wave T2. Since the technique of generating the electrical signal corresponding to the terahertz wave T2 is generally used in the field of terahertz waves, a detailed description thereof will be omitted.

The electrical signal oscillated by the terahertz wave receiver 53 may be transmitted to the signal amplifier 55 through the waveguide 57 provided to connect the terahertz wave receiver 53 and the signal amplifier 55.

The signal amplifier 55 may amplify the electrical signal received through the waveguide 57 at a predetermined amplification rate, cancel noise included in the electrical signal using the modulated signal received from the signal modulator 43, and transmit the same to the controller 60.

The controller 60 may be provided to generally control driving of the water-proofing test device 1.

The controller 60 may determine whether water has penetrated into the test area A by analyzing the frequency spectrum of the terahertz wave T2, and test water-proofing performance of the test target P based on whether water has penetrated into the test area A. In other words, when it is determined that water has not penetrated into the test area A, the controller 60 determines that the water-proofing performance of the test target P is normal, and when it is determined that water has penetrated into the test area A, the controller 60 determines that the water-proofing performance of the test target P is not normal. Here, a change in the electrical signal oscillated by the terahertz wave receiver 53 may indicate a change in the electromagnetic field of the terahertz wave T2. Thus, the controller 60 may analyze the frequency spectrum of the terahertz wave T2 through analysis of the electrical signal received from the signal amplifier 55 over time. To this end, the controller 60 may control the dual mode laser beam oscillator 41 of the terahertz wave oscillator 40 such that the frequency of the terahertz wave T1 may be gradually converted within a predetermined frequency band including at least one of peak frequencies F1, F2, and F3.

A method of analyzing the frequency spectrum of the terahertz wave T2 is not particularly limited.

For example, the controller 60 may determine whether water has penetrated into the test area A by comparing power A1, A2, and A3 of the terahertz wave T2 at the peak frequencies F1, F2, and F3 with power of the terahertz wave T2 in the other remaining frequency bands excluding the peak frequencies F1, F2, and F3.

When water has penetrated into the test area A, water vapor generated as water which has penetrated into the test area A is evaporated by the evaporator 30 may be received in the test area A. Accordingly, the terahertz wave T2 of the peak frequencies F1, F2 and F3 may be absorbed by water vapor received in the test area A at a relatively higher rate, compared to the terahertz wave T2 in the other remaining frequency bands, in the process of being reflected from the test area A. Thus, as illustrated in FIG. 7, when water has penetrated into the test area A, the power of terahertz wave T2 tends to be measured to be significantly low at the peak frequencies F1, F2, and F3, compared to the other remaining frequency bands. That is, as illustrated in FIG. 7, when water has penetrated into the test area A, there is a water vapor absorption peak K, which is generated as the power A1, A2, and A3 of the terahertz wave T2 at the peak frequencies F1, F2, and F3 is significantly lower than the power of the terahertz wave T2 in the other remaining frequency bands, in the frequency spectrum of the terahertz wave T2. Thus, if the water vapor absorption peak K does not exist in the frequency spectrum of the terahertz wave T2, the controller 60 may determine that water has not penetrated into the test area A, and if the water vapor absorption peak K exists in the frequency spectrum of the terahertz wave T2, the controller 60 may determine that water has penetrated into the test area A. In other words, the controller 60 may determine whether an abnormality occurs in the water-proofing performance of the test target P depending on whether the water vapor absorption peak K exists in the frequency spectrum of the terahertz wave T2.

For example, the controller 60 may determine whether water has penetrated into the test area A on the basis of the power A1, A2, and A3 of the terahertz wave T2 at the peak frequencies F1, F2, and F3.

To this end, the controller 60 may calculate a difference between reference power R1, R2, and R3 previously measured from a reference sample as in a reference example of FIG. 7 and the power A1, A2, and A3 (hereinafter, referred to as "actually measured power") of the terahertz wave T2 at the peak frequencies F1, F2, and F3 measured from the test area A of the test target P in real time as in some forms of FIG. 7. The reference sample refers to a sample which has the same structure as that of the test target P and into which water does not penetrate. The reference power R1, R2, and R3 refers to power of the terahertz wave T2 at the peak frequencies F1, F2, and F3 previously measured from a specific area of the reference sample corresponding to the test area A of the test target p. When the actually measured power A1, A2, and A3 is lower than the reference power R1, R2, and R3 by a predetermined reference ratio, the controller 60 may determine that water has penetrated the test area A. In addition, the controller 60 may estimate an amount of water which has penetrated into the test area A on the basis of absolute magnitudes of the actually measured power A1, A2, and A3. In this manner, the controller 60 may estimate the degree of abnormality in the water-proofing performance of the test target P on the basis of the estimated amount of water.

Meanwhile, the controller 60 may display an image of the determined water-proofing test result on the display unit 26 of the measurement probe 20, thereby providing the result to the operator in real time.

The water-proofing test device 1 may perform a water-proofing test on the test target P all over the inside and outside of the test target P using transmission of the terahertz wave T1. Thus, the water-proofing test device 1 may easily detect even water penetrating into the inside of the test target P which is difficult to observe from the outside, such as a gap between the vehicle body frame P1 and the protective layer P2, thereby improving accuracy of the water-proofing test. Furthermore, the water-proofing test device 1 may test the water-proofing performance of the test target P in a non-destructive state, without having to disassemble the test target P. Therefore, the water-proofing test device 1 may reduce time required for the water-proofing test, and prevent secondary damage which may be done to the test target P in the course of disassembling and assembling the test target P for the water-proofing test.

The water-proofing test device 1 includes the evaporator 30 capable of phase-transforming water penetrating into the test target P into water vapor. Thus, the water-proofing test device 1 may perform the water-proofing test using the terahertz wave having the peak frequencies F1, F2, and F3 at which an energy absorption rate by water vapor is remarkably high in the terahertz frequency band, whereby accuracy of the water-proofing test may be further enhanced.

Meanwhile, it has been described that the water-proofing test device 1 performs the water-proofing test on the test target P by analyzing the terahertz wave T2 reflected from the test area A, but the present disclosure is not limited thereto. That is, the water-proofing test device 1 may perform the water-proofing test on the test target P by analyzing the terahertz wave T2 transmitted through the test area A. In this case, the water-proofing test device 1 may further include at least one optical path changing member such as a reflector so that the terahertz wave T2 transmitted through the test target P may be transmitted to the terahertz wave detector 50.

Figure 8:
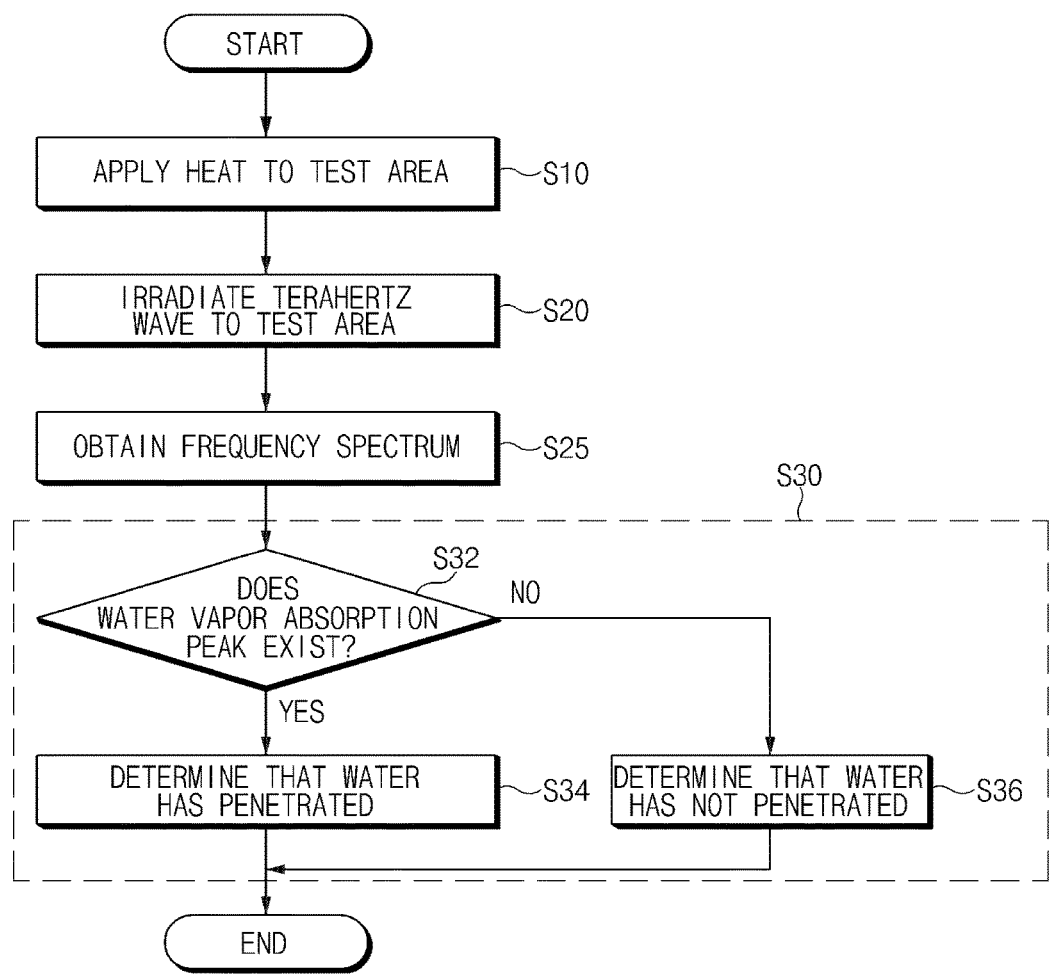
FIG. 8 illustrates a flowchart of a method for a water-proofing test, in one form of the present disclosure.

FIG. 8 illustrates a flowchart of a method for a water-proofing test, in some forms of the present disclosure.

The method for a water-proofing test, in some forms of the present disclosure, may include: applying heat to the test area A such that water penetrating into the predetermined test area A of the test target P is evaporated to be phase-transformed to water vapor in operation S10, irradiating the terahertz wave T1 to the test area A in operation S20; and analyzing the terahertz wave T2 reflected from the test area A or transmitted through the test area A to determine whether water has penetrated into the test area A in operation S30.

First, operation S10 may be performed by irradiating the guide laser beam G oscillated from the guide laser beam oscillator 32 to the test area A so as to evaporate water penetrating into the test area A. Here, when water penetrates into the test area A, the water penetrating into the test area A may be evaporated by heat applied from the guide laser beam G and be phase-transformed to water vapor.

Next, operation S20 may be performed by irradiating the terahertz wave T1, generated by converting the pair of distributed feedback laser beams B1 and B2 beat and oscillated from the dual mode laser beam oscillator 41 using the terahertz wave transmitter 45, to the test area A. Operation S20 may be performed by controlling the dual mode laser beam oscillator 41 such that the frequency of the terahertz wave T1 may be gradually changed within a predetermined frequency band including at least one of peak frequencies F1, F2, and F3. Then, the terahertz wave T1 irradiated to the test area A, in a state of being absorbed by water vapor generated in operation S10 at an absorption rate corresponding to the frequency, may be reflected from the test area A or transmitted through the test area A.

Thereafter, operation S30 may be performed by determining whether water has penetrated into the test area A through the analysis of a frequency spectrum of the terahertz wave T2 reflected from the test area A or transmitted through the test area A. To this end, as illustrated in FIG. 8, the water-proofing test method may further include obtaining the frequency spectrum of the terahertz wave T2 reflected from the test area A or transmitted through the test area A in operation S25, which is performed between operation S20 and operation S30.

A method of analyzing the frequency spectrum of the terahertz wave T2 is not particularly limited.

For example, in operation S30, it may be determined whether water has penetrated into the test area A by comparing power A1, A2, and A3 of the terahertz wave T2 at at least one of the peak frequencies F1, F2, and F3 with power of the terahertz wave T2 in the other remaining frequency bands excluding the peak frequencies F1, F2, and F3. To this end, as illustrated in FIG. 8, operation S30 may include: determining whether the water vapor absorption peak K exists in the frequency spectrum in operation S32; determining that water has penetrated into the test area A when the water vapor absorption peak K exists in the frequency spectrum in operation S34; and determining that water has not penetrated into the test area A when the water vapor absorption peak K does not exist in the frequency spectrum in operation S36.

For example, operation S30 may be performed by determining whether water has penetrated into the test area A on the basis of the power A1, A2, and A3 of the terahertz wave T2 at at least one of the peak frequencies F1, F2, and F3. More specifically, operation S30 may be performed by determining that water has penetrated into the test area A if the power A1, A2, and A3 of the terahertz wave T2 at the peak frequencies F1, F2, and F3 measured from the test area A is lower than the previously stored reference power R1, R2, and R3 by a predetermined reference ratio or higher.

As set forth above, the device and method for a water-proofing test, in some forms of the present disclosure, have the following effects:

First, since water penetrating into the inside of an object to be tested (or test target), which is difficult to observe from the outside, is detected using transmission of the terahertz wave, accuracy of the water-proofing test may be improved;

Second, since water-proofing performance of a test target is tested in a non-destructive state of the test target, time required for the water-proofing test may be reduced and secondary damage which may be done to the object in the process of disassembling and assembling the test target may be prevented; and Third, since the water-proofing test is performed using the properties of the terahertz wave in which an energy absorption peak where an energy absorption rate by water vapor is remarkably high at a specific frequency exists, accuracy of the water-proofing test may be further improved.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:
1. A device for a water-proofing test, the device comprising:
  a terahertz wave oscillator configured to generate and oscillate a terahertz wave;
  a terahertz wave detector configured to detect the terahertz wave reflected from a predetermined test area of a test target or transmitted through the predetermined test area; and a controller configured to analyze a frequency spectrum of the terahertz wave detected by the terahertz wave detector to determine whether water is penetrated into the predetermined test area,
wherein the terahertz wave oscillator further comprises a terahertz wave collector configured to:
  collect the terahertz wave;
  transmit the terahertz wave to a terahertz wave receiver;
  have an integrating sphere formed of a material capable of reflecting the terahertz wave; and
  have a predetermined radius of curvature.

2. The device of claim 1, wherein the device further comprises:
an evaporator configured to apply heat to the predetermined test area such that the water is phase-transformed into water vapor.

3. The device of claim 2, wherein the evaporator comprises:
a guide laser beam oscillator configured to generate and oscillate a guide laser beam for evaporating the water; and
a guide laser beam irradiator configured to irradiate the guide laser beam to the predetermined test area.

4. The device of claim 2, wherein the terahertz wave oscillator is configured to oscillate the terahertz wave when the evaporator applies the heat to the predetermined test area.

5. The device of claim 2, wherein the controller is configured to determine whether the water is penetrated into the predetermined test area by comparing power of the terahertz wave having at least one peak frequency with power of the terahertz wave having remaining frequency bands excluding the at least one peak frequency, wherein, in the at least one peak frequency, an absorption rate of the terahertz wave by the water vapor is greater than or equal to a predetermined rate.

6. The device of claim 5, wherein the controller is configured to control the terahertz wave oscillator such that a frequency of the terahertz wave is converted within a predetermined frequency band including the at least one peak frequency.

7. The device of claim 2, wherein the controller is configured to determine whether the water is penetrated into the predetermined test area based on the power of the terahertz wave having the at least one peak frequency.

8. The device of claim 1, wherein the terahertz wave oscillator comprises:
a dual mode laser beam oscillator configured to generate and oscillate a pair of distributed feedback laser beams having different wavelengths; and
a terahertz wave transmitter configured to generate and oscillate the terahertz wave upon receiving the distributed feedback laser beams.

9. The device of claim 8, wherein:
the terahertz wave receiver is configured to:
  convert the terahertz wave into an electrical signal, wherein the terahertz wave is reflected from the predetermined test area or is transmitted through the predetermined test area; and
  oscillate the electrical signal.

10. The device of claim 9, wherein the terahertz wave detector further comprises:
a signal amplifier configured to:
  amplify the electrical signal; and
  transmit the electrical signal to the controller.

11. The device of claim 1, wherein;
the terahertz wave receiver is positioned at a focal point of the terahertz wave collector.

12. A method for a water-proofing test using a device for the water-proofing test, the method comprising steps of:
(a) applying heat to a predetermined test area of a test target such that water penetrating into the predetermined test area is phase-transformed into water vapor;
(b) irradiating a terahertz wave to the predetermined test area; and
(c) analyzing the terahertz wave reflected from the predetermined test area or transmitted through the predetermined test area to determine whether water is penetrated into the predetermined test area,
wherein the device for the water-proofing test comprises:
  a terahertz wave oscillator configured to generate and oscillate a terahertz wave;
  a terahertz wave detector configured to detect the terahertz wave reflected from the predetermined test area or transmitted through the predetermined test area;
  a controller configured to analyze a frequency spectrum of the terahertz wave to determine whether the water is penetrated into the predetermined test area,
wherein the terahertz wave oscillator comprises a terahertz wave collector configured to:
  collect the terahertz wave;
  transmit the terahertz wave to a terahertz wave receiver;
  have an integrating sphere formed of a material capable of reflecting the terahertz wave; and
  have a predetermined radius of curvature.

13. The method according to claim 12, further comprising a step of:
(d) obtaining a frequency spectrum of the terahertz wave, wherein step (d) is performed after step (b) and before step (c), and
wherein the step (c) comprises analyzing a frequency spectrum of the terahertz wave to determine whether the water is penetrated into the predetermined test area.

14. The method of claim 12, wherein step (a) comprises:
irradiating a guide laser beam to evaporate the water to the predetermined test area.

15. The method of claim 12, wherein the step (b) comprises:
converting a frequency of the terahertz wave within a predetermined frequency band including at least one peak frequency, wherein, in the at least one peak frequency, an absorption rate of the terahertz wave by the water vapor is greater than or equal to a predetermined rate.

16. The method of claim 15, wherein the step (c) comprises:
determining whether the water is penetrated into the predetermined test area by comparing power of the terahertz wave having at least one peak frequency with power of the terahertz wave having remaining frequency bands excluding the at least one peak frequency.

17. The method of claim 15, wherein the step (c) comprises:
determining whether the water is penetrated into the predetermined test area based on the power of the terahertz wave having the at least one peak frequency.

* * * * *